United States Patent [19]

Roth et al.

[11] Patent Number: 4,776,151

[45] Date of Patent: Oct. 11, 1988

[54] PACKAGE HAVING FIBER-CONTAINING SHEATH AND APPARATUS AND METHOD FOR PACKAGING

[75] Inventors: Nathan Roth, San Francisco; Andrew Nelsen, Palo Alto, both of Calif.

[73] Assignee: ALZA Corporation, Palo Alto, Calif.

[21] Appl. No.: 89,633

[22] Filed: Aug. 25, 1987

[51] Int. Cl.4 .................. B65B 15/04; B65B 49/04; B65B 11/08

[52] U.S. Cl. ...................... 53/435; 53/450; 53/520; 53/522; 53/545; 53/547

[58] Field of Search ............ 53/450, 462, 466, 455, 53/449, 170, 550, 562, 236, 435, 522, 51, 520, 545, 547

[56] References Cited

U.S. PATENT DOCUMENTS

| | | | |
|---|---|---|---|
| 2,113,078 | 4/1938 | Campbell | 53/450 X |
| 2,406,018 | 8/1946 | Irmscher | 53/450 X |
| 2,435,347 | 2/1948 | Gilman | 53/450 X |
| 2,539,395 | 1/1951 | Banks | 53/450 X |
| 3,561,187 | 2/1971 | Rohnert et al. | 53/450 X |
| 3,655,478 | 4/1972 | Geschwender | 53/450 X |
| 3,960,350 | 1/1976 | Reid | 53/455 X |
| 4,079,568 | 3/1978 | Wortman | 53/435 X |
| 4,144,317 | 3/1979 | Higuichi et al. | 424/21 |
| 4,175,326 | 11/1979 | Goodson | 433/80 |
| 4,372,098 | 2/1983 | Mason | 53/449 X |
| 4,646,510 | 3/1987 | McIntyre | 53/449 |

Primary Examiner—Horace M. Culver
Attorney, Agent, or Firm—Shelly G. Precivale; Edward L. Mandell; Steven F. Stone

[57] ABSTRACT

The package of the present invention comprises a sheath formed from a folded, relatively rigid strip having structure for receiving and releasably holding the ends of the fiber to be packaged. In a preferred embodiment, the fiber is between the two folded over parts of the strip with the ends of the fiber anchored in place in a pair of slits. The sheath is in a pouch formed by a pair of foil members on opposite sides of the sheath. When ready for use, the package is opened by peeling the foil members apart, thereby exposing the sheath and permitting access to the fiber carried by the sheath. An improved apparatus and method are provided to form the package. In the first instance, the sheath is prepared by first folding a strip of relatively rigid material, such as siliconized polyester, then moving the folded strip along a path of travel and feeding the fiber into the region between the parts of the strip as the strip moves. At a certain location along the path of the strip, the fiber is forced into each slit of the strip and the fiber becomes releasably attached to the strip. At another location, the strip is cut; thus, in this way, a plurality of sheaths with fiber lengths between the sides of the sheaths are formed and are immediately moved to a location where the foil members are applied to the opposite sides of the sheaths.

35 Claims, 4 Drawing Sheets

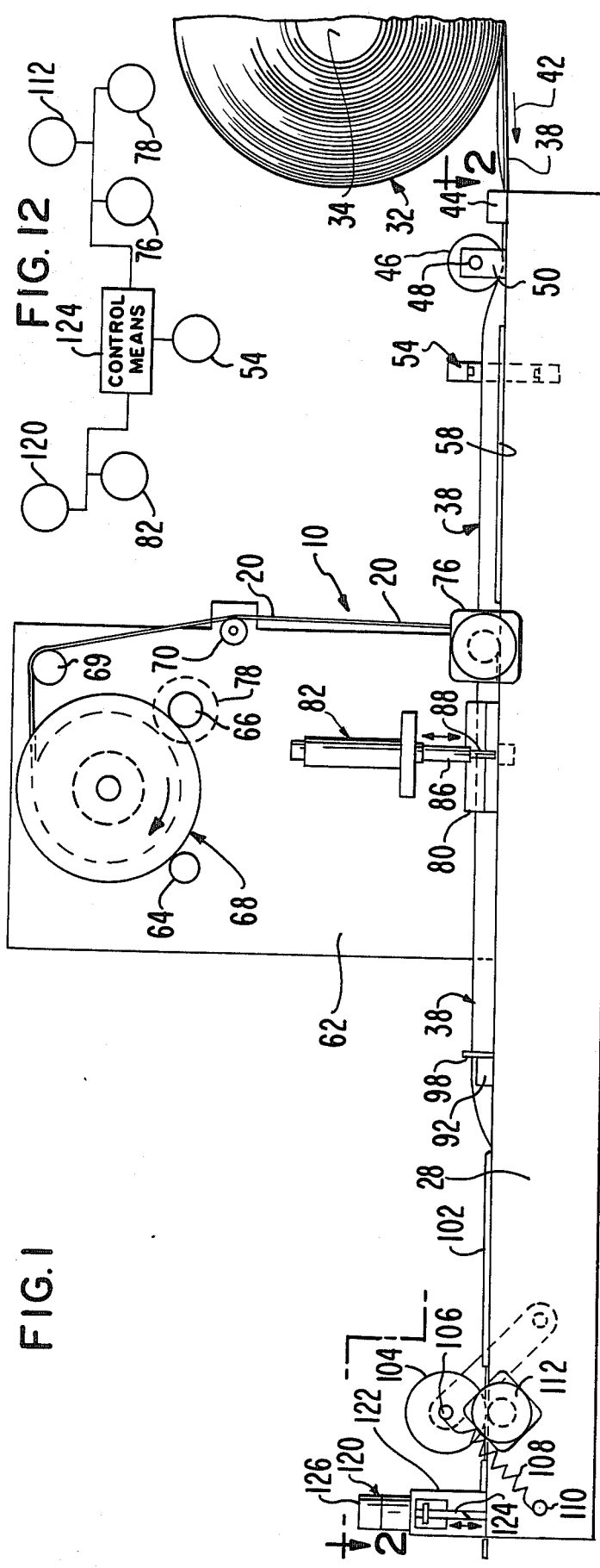

PACKAGE HAVING FIBER-CONTAINING SHEATH AND APPARATUS AND METHOD FOR PACKAGING

This invention relates to in the packaging of elongated flexible members and, more particularly, to a package containing a flexible fiber or strand and to an apparatus and method for packaging the fiber.

BACKGROUND OF THE INVENTION

It has been found that a medicinal preparation can be applied in a periodontal sense to the teeth and gums by the use of an elongated, flexible, stretchable fiber which incorporates a medicinal preparation. The fiber is used by wrapping it around the base of a tooth near the gum line to apply the medicinal preparation. Such fibers are disclosed in U.S. Pat. Nos. 4,144,317 and 4,175,326, and these patents are incorporated herein by reference.

While such fibers are highly satisfactory media for applying the medicinal preparation as described above, a problem arises in the handling of the fiber before use particularly if it is to be provided as an individual unit dosage rather than bulk packaged on a spool, for example. The fiber is difficult to package because of its adhesive qualities, thermo-sensitivity and handling requirements. Because of these problems, a need exists for a package for a fiber of the type described as well as apparatus and method for quickly and economically forming the package. The present invention satifies this need by providing a novel package which affords adequate protection for the fiber while providing easy access to the fiber when it is ready for use.

SUMMARY OF THE INVENTION

The package of the present invention comprises a sheath formed from a folded, relatively rigid strip having spaced means for receiving and releasably holding the ends of the fiber to be packaged. In a preferred embodiment, the fiber is between the two folded over parts of the strip with the ends of the fiber anchored in place in a pair of slits. The sheath is in a pouch formed by a pair of foil members on opposite sides of the sheath, the foil members being heat sealed or otherwise secured together to form a sealed region in which the sheath is located. When ready for use, the package is opened by peeling or tearing open the foil members away from each other, thereby exposing the sheath and permitting access to the sheath and the fiber carried thereby.

An improved apparatus and method are provided to form the package. In the first instance, the sheath is prepared by first folding the strip of relatively rigid material, such as siliconized polyester, then moving the folded strip along a path of travel and coupling the fiber to the strip, such as by feeding the fiber into the region between the parts of the strip as the strip moves. At a certain location along the path of travel of the strip, the fiber is forced into each slit of the strip and the fiber becomes releasably attached to the strip itself between the folded over parts of the strip.

At another location along the path of travel of the strip, the strip is cut; thus, in this way, a plurality of sheaths with fiber lengths between the sides of the sheaths are formed and are immediately moved to a location where the foil members are applied to the opposite sides of the sheaths. The practice of the method of the present invention provides a high production rate yet the fiber in each package is adequately protected from contamination and is immediately ready for use when the package is opened, all of which can be achieved without diminishing the medicincal benefits provided by the medicinal substance impregnated in th fiber.

The primary object of the present invention is to provide a package for a flexible fiber which is generally difficult to package because of its flexibility, size and other qualities wherein the fiber is contained in a sheath formed from a foldable, relatively rigid strip having means at the ends thereof for releasably coupling itself to the ends of the fiber with the sheath being contained in a pouch which can be heat-sealed and opened when the fiber is ready for use, whereby the fiber is adequately protected against contamination yet the fiber can be quickly and easily made ready for use by exposing the sheath and separating the fiber from the sheath.

Another object of the present invention is to provide an improved apparatus and method for forming a package of the type described wherein the package can be made quickly and easily and inexpensively yet the production rate of making the package can be relatively high notwithstanding the need to accurately position the fiber in a relatively narrow sheath and to secure the ends of the fiber to the sheath while the sheath and fiber are being moved together along a predetermined path at a given rate.

Other objects of this invention will become apparent as the following specification progresses, reference being had to the accompanying drawings for an illustration of the invention.

In the Drawings

FIG. 1 is a side elevational view, partly schematic, of the packaging apparatus of the present invention;

FIG. 2 is a cross-sectional view taken along line 2—2 of FIG. 1;

FIG. 12 is a schematic view of a control means for the apparatus of FIG. 1.

Figure 1A:
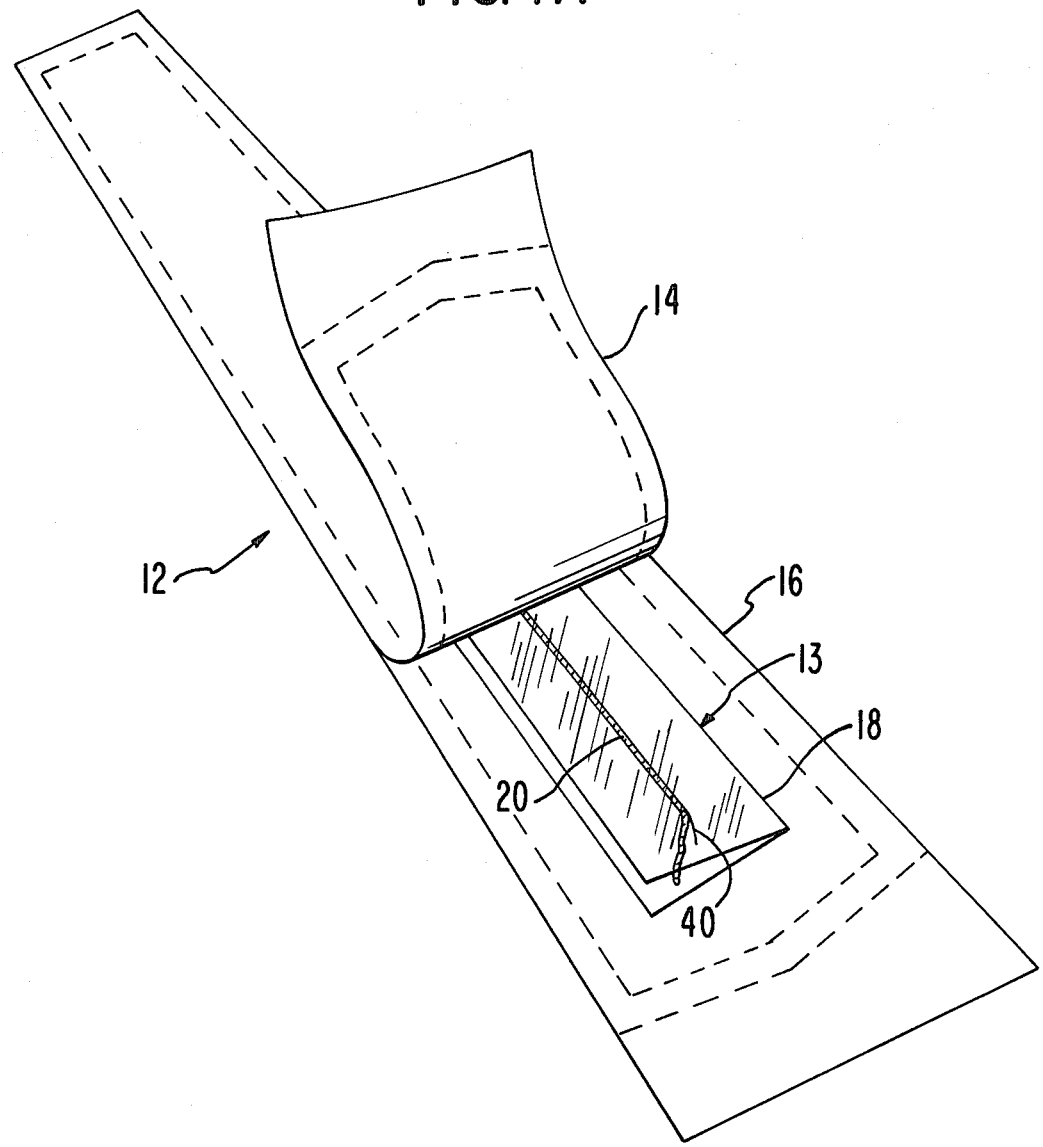
FIG. 1A is a perspective view of a package containing a sheath formed by the apparatus of FIG. 1.

The packaging apparatus of the present invention is broadly denoted by the numeral 10 and is illustrated in FIGS. 1-6. Machine 10 is adapted, when an operation, to form a fiber-containing sheath 18 which is part of a package 12 (FIG. 1A) defined by a pair of outer foil strips 14 and 16 between which is sandwiched the sheath 18 containing an elongated, flexible fiber or strand 20. For purposes of illustration, the fiber is formed from a stretchable, polymeric material and is impregnated with a medicinal component, such as a periodontal therapeutic substance. A primary function of the apparatus 10 is to form sheath 18 from a plastic strip and to place fiber 20 within the sheath, following which the fiber-containing sheath is placed between the two foil members 14 and 16 and the foil members are heat sealed or otherwise fastened at their outer peripheries to enclose the sheath and fiber within the foil members to form package 12. The package can then be stored along with other such packages until ready for use. To open the package, the foil members 14 and 16 are separated from each other (as as shown in FIG. 1A) by peeling one away from the other so as to gain access to sheath 18 containing fiber 20. The fiber can then be removed from the sheath and used for the purpose for which the fiber is designed.

Figure 4:
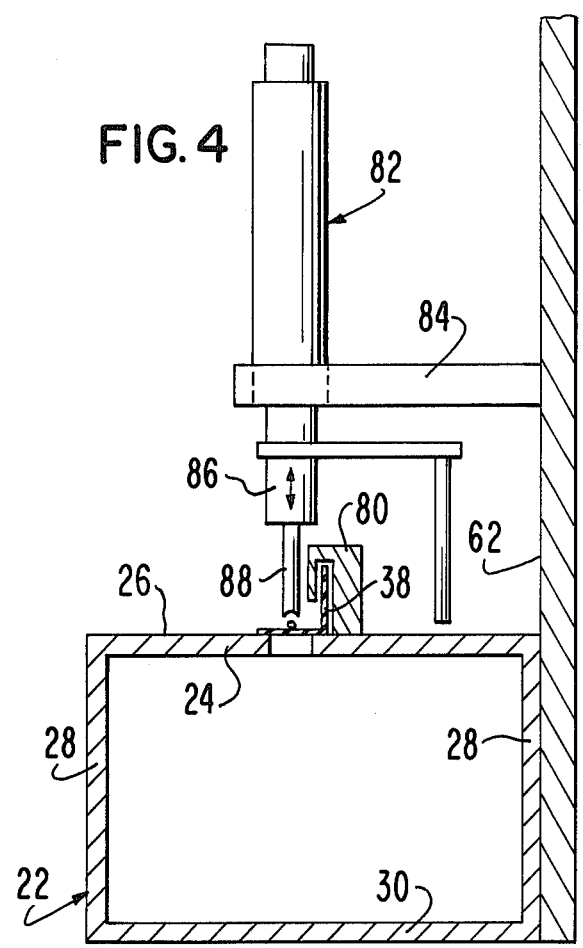
FIG. 4 is an enlarged, cross-sectional view taken line 4—4 of FIG. 2.

Apparatus 10 includes an elongated support 22 which, for purposes of illustration, is a box beam as shown in FIGS. 1, 2 and 4. Support 22 includes a top wall 24 provided with an upper surface 26 as shown in FIG. 4. The support also includes a pair of opposed sides 28 and a bottom 30 which is adapted to rest upon a table or other surface.

Figure 7A:
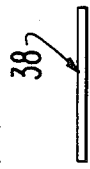
FIGS. 7 and 7A are plan and end views, respectively, of the polyester strip which is used to form the sheath of the package of FIG. 1A.

A reel 32 is rotatably mounted by a shaft 34 on support 22 in any suitable manner near the upstream end 36 of the support (FIGS. 1 and 2). Reel 42 is adapted to contain a roll of a suitable sheath-forming material, such as siliconized polyester, which typically is relatively rigid and transparent and, for purposes of illustration, is about 1.5 inches in width. The strip 38 is shown in more detail in FIGS. 7 and 7A and the strip has shaded segments 39 at equally spaced locations on the strip. The segments are integral with the strip and can be applied thereto in any suitable manner, such as by a photographic or printing process. Each of the segments has a detectable characteristic, such as less light transmissivity or a differing magnetic or physical characteristic than the remainder of the strip. Thus, the segments can serve as index marks to interrupt a light beam of a photoelectric, magnetic or other device as hereinafter described.

Each segment is provided with a curved slit 40 which is preferably precut in the strip 38 before the strip is placed on reel 32. Each slit 40 is closer to one side edge of the strip than to the other side. Also, each slit is adapted to releasably receive and anchor a particular end of a length of fiber 20 when an adjacent length of strip 38 has been cut and forms the sheath 18 (FIG. 12) of a package 12. Other means, such as an adhesive or a heat tack, can be used to anchor the fiber to the sheath 18.

Figure 8A:
FIGS. 8 and 8A are views similar to FIGS. 7 and 7A but showing the strip folded into halves.
Figure 8:
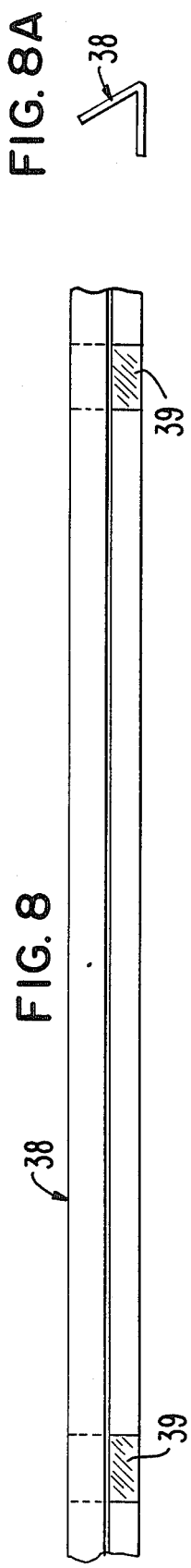

Strip 38 is movable off reel 32 in the direction of arrow 42 (FIGS. 1 and 2) and, as it moves, the strip passes over a folding device 44 which folds the strip into two parts, preferably into halves, the fold being shown in FIGS. 8 and 8A. To assist in obtaining a uniform fold, strip 38 is preferably provided with a longitudinally extending partial perforation 41 or score line along the fold. It has been found that a sewing machine hemmer is suitable for the purpose in folding strip 38. The folding causes a crease in the strip along the perforation 41, and this crease becomes essentially a permanent set by moving the folded strip beneath a bearing roller 46 rotatably mounted by a shaft 48 on spaced bearings 50 on support 22 as shown in FIGS. 1 and 2.

Figure 9A:
FIGS. 9 and 9A are views similar to FIGS. 8 and 8A but showing a fiber placed on one of the halves of the strip with spaced parts of the fiber being in spaced slits in the strip.
Figure 10A:
FIGS. 10 and 10A are views similar to FIGS. 9 and 9A, respectively, but showing the strip completely folded over to encase the fiber therewithin and to form the sheath.

Apparatus 10 further includes a guide 52 which retains and guides the upper half of strip 38 while it retains the lower half near the upper surface 26 of support 22. FIG. 9A shows the way in which one half of strip 38 is substantially vertical and held in that position by guide 52.

A detecting device 54, such as a photoelectric device, is carried by support 22 downstream from the upstream end of guide 52. Device 54 includes a light source 56 and a photodetector 58 aligned with light source 56 for receiving a light beam 60 from light source 56, the light source being below surface 26 and detector 58 being above the surface, there being an opening 62 in top wall 24 of support 22 for allowing the light beam 60 to pass normally upwardly to detector 58. Breaking of the light beam by a segment 39 of strip 38 causes a signal to be generated by control means 124 (FIG. 12) and such signal is directed to several drive motors as hereinafter described which synchronize the movements of strip 38 and fiber 20 as they move simultaneously longitudinally of the support 22.

Figure 3:
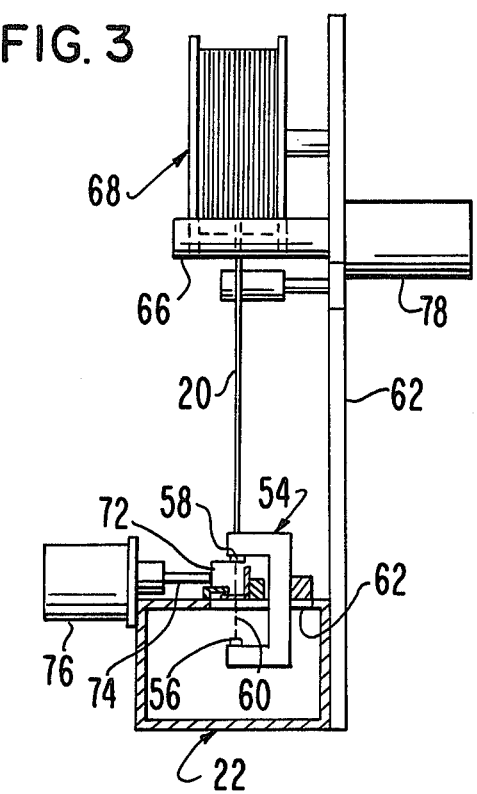
FIG. 3 is an enlarged, cross-sectional view taken along line 3—3 of FIG. 2.

Guide 52 includes a pair of side-by-side rails 56 and 58 which are spaced apart to present a space 60 through which one half of strip 38 passes while the other strip is parallel to the upper surface 26 of support 22 as shown in FIG. 3.

An upright panel 62 is rigidly secured to support 22 and extends upwardly therefrom near one side 28 thereof as shown in FIGS. 1, 2 and 4. Panel 62 has a pair of spaced rollers 64 and 66 mounted thereon for rotation about respective horizontal axes. The rollers extend outwardly from the panel 62 above the path of travel of strip 38. These rollers are adapted to support and to rotate a reel 68 of fiber 20 which pays off reel 68 and over a third roller 69, past an idler 70 and then downwardly and partially about a roller 72 on the shaft 74 of a stepper motor 76 rigidly secured to and extending laterally from one side of support 22 as shown in FIG. 2.

A second stepper motor 78 is carried by panel 62 in any suitable manner, such as at a location shown in FIG. 3. Moto 78 is coupled with roller 66 for rotating the same, whereby reel 68 can be driven in a clockwise sense when viewing FIG. 1. Roller 69 is coupled with motor 78 by an endless, flexible band (not shown) to rotate at a tangential velocity greater than that of reel 68. This assures that there will be tension on fiber 20 as it comes off reel 68.

Fiber 20 extends downwardly and about roller 72 and is urged by the roller in a downstream direction as indicated by arrow 79 (FIG. 2).

A guide member 80 is mounted on upper surface 26 in any suitable manner, the guide member having an inverted J-shaped configuration as shown in FIG. 4. The guide member 80 serves to channel one half of strip 38 vertically as the strip moves longitudinally of the support and as the other half of the strip is adjacent to and is generally parallel with the upper surface 26 of support 22 (FIG. 4).

A fluid piston and cylinder assembly 82 is coupled by a bracket 84 on panel 62 as shown in FIG. 4. Assembly 82 has a piston rod 86 having a tool 88 on the lower end thereof, the tool having a concave space 90 (FIG. 4) which presents a generally inverted U-shaped configuration, the purpose of which is to trap fiber 20 within the concave space 90 as tool 88 moves downwardly to force the fiber into a slit 40 (FIG. 7) aligned with the tool as hereinafter described. The tool could have any one of several other configurations, such as a flat bottom surface.

Figure 9:
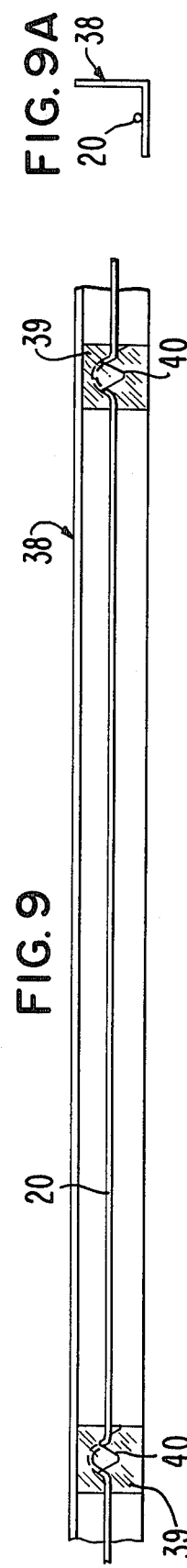
Figure 10:
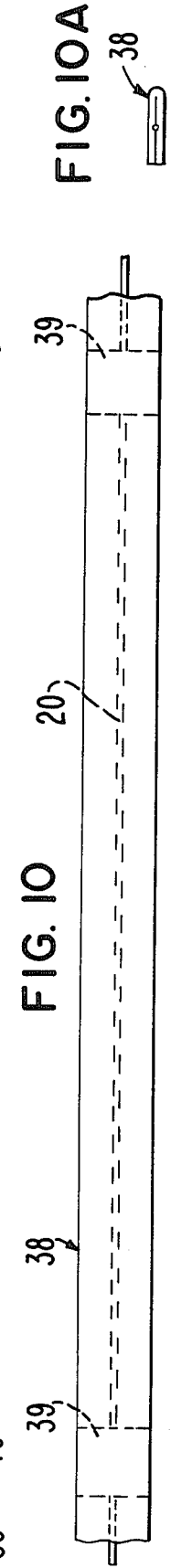

When the tool pushes the fiber 20 into an adjacent slit 40, the fiber becomes hooked or releasably held in the slit as shown in FIG. 9, whereupon the fiber is connected at various locations along the strip 38, specifically at locations adjacent to segments 39. Upon being cut at each of these segments, the strip 38 is severed into individual lengths, such as 12 to 15 inch lengths, which define sheaths 18 of the type shown in FIG. 11.

Figure 5:
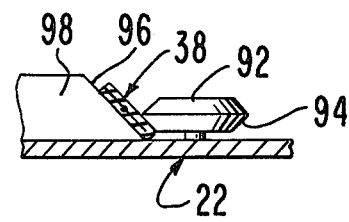
FIG. 5 is an enlarged, cross-sectional view taken along line 5—5 of FIG. 2.
Figure 6:
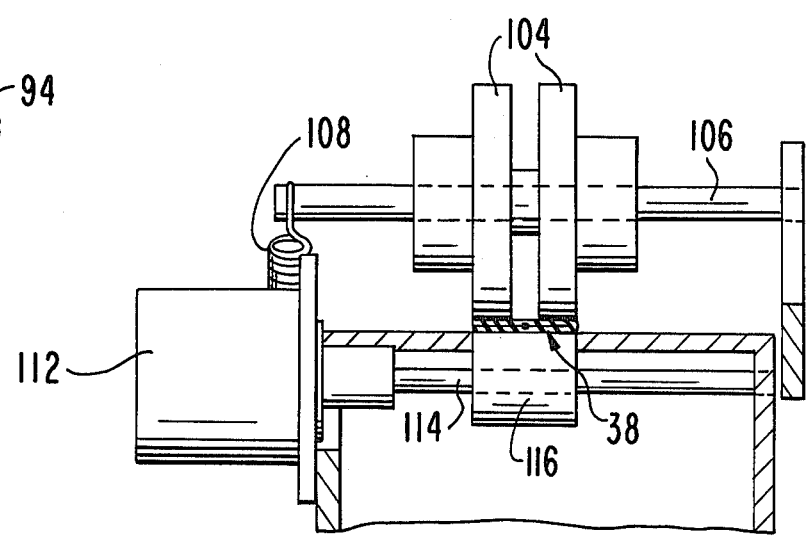
FIG. 6 is an enlarged, cross-sectional view taken along line 6—6 of FIG. 2.

A pair of guides engageable with strip 38 are provided downstream of tool 88 as shown in FIGS. 1, 2 and 5. The purpose of these guides is to substantially remove any wrinkles in the strip. These guides include a first guide 92 which has a bevelled, circular lower surface 94 (FIG. 5) for engaging the backside of the vertical half of strip 38 to bend it over and to cause it to meet the other half of the strip which is moved along an inclined surface 96 of a second guide 98 on the opposite side of the path of the strip as shown in FIGS. 2 and 5. Guide 98 is in the form of a plate which is secured in any suitable manner to support 22 and extends upwardly from upper surface 26.

A pair of spaced, parallel rails 100 and 102 are located downstream of guides 92 and 98 as shown in FIG. 2. Rails 100 and 102 serve as guides for guiding the folded strip 38, with its halves juxtaposed, to a location beneath a pair of rollers 104 mounted on a shaft 106 which is biased to the left when viewing FIG. 2 by a coil pring 108, one end of the spring being coupled to the shaft 106 and the opposite end of the spring being coupled to a pin 110 projecting laterally from support 22. A stepper motor 112 carried by support 22 has a drive shaft 114 (FIG. 6) coupled to a pressure roller 116 beneath rollers 104, and roller 116 drives the folded-over strip 38 with the fiber 20 therebetween in a downstream direction.

A strip cutting device 120 is secured by a bracket 122 on support 22 downstream of roller 104, and the cutting device 120 has a shaft 124 coupled to a piston and cylinder assembly 126, the lower end of the shaft forming a cutting blade and being movable downwardly and into cutting relationship with strip 38 therebeneath. The cutting of the strip occurs after movement of strip 38 has been stopped, i.e., by stopping the stepper motor 112 and thereby drive roller 116 (FIG. 6) which drives the strip 38 in the downstream direction. The cutting action occurs when a segment 39 is directly beneath the cutting blade 124 and the cutting blade cuts segment 39 widthwise in half. Simultaneously, the cutting blade cuts fiber 20 so that the end of the cut strip appears as shown to the left of FIG. 11.

Figure 11:
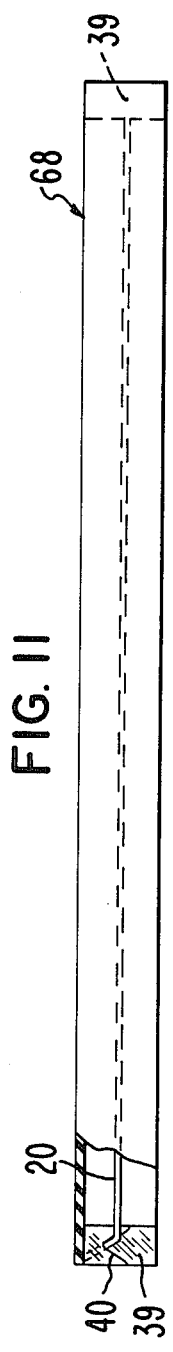
FIG. 11 is a view similar to FIG. 10 but showing the strip severed into a predetermined length and showing one end of the fiber held in an adjacent slit of the strip.

Cutting of the next segment 39 in half along with fiber 20 forms sheath 18 with a single length of fiber 20 in the sheath and with the end of the fiber in respective end slots 40 of the sheath (FIG. 11).

The three stepper motors 76, 78 and 112 are synchronized in that they are parts of a control means 124 (FIG. 12) responsive to photoelectric device 54 so that, each time a segment 39 passes device 54, the three stepper motors are deactivated, tool assembly 82 and cutter assembly 126 are actuated, tool 88 poking or forcing fiber 20 into the slot 40 of the adjacent segment 39 while cutter blade 124 severs the strip and fiber 20 so as to cut the adjacent segment 39 into two parts. Then, control means 124 will be further actuated after a predetermined time delay to actuate the three stepper motors again until the next segment 39 comes into position aligned with the photoelectric device 54.

Figure 7:
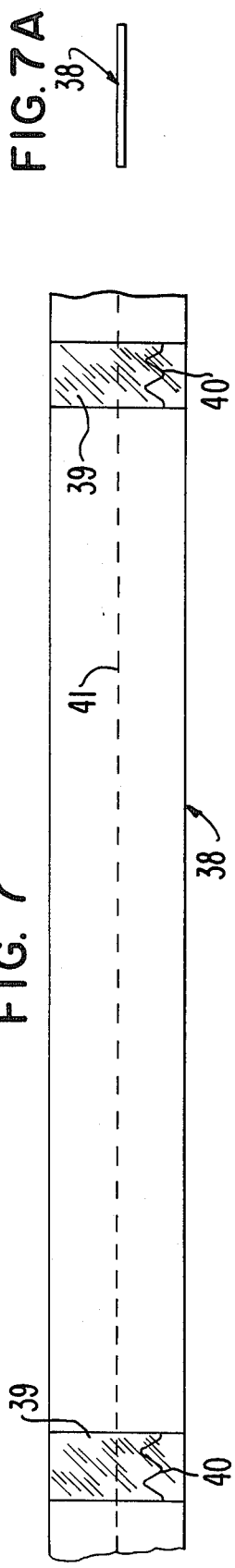

In the operation of apparatus 10, strip 32 will be on reel 32 on shaft 34, and the strip will be threaded through the apparatus until the end of the strip is downstream of rollers 104 and drive motor 112. The strip 38 will preferably have been previously printed or otherwise processed to form the segments 39. Moreover, the strip will have been precut at each segment 39 to form a slit 40 at each segment 39, each slit being closer to one side edge of strip 30 than to the other side edge as shown in FIG. 7 and pre-perforated with partial perforation 41. Alternatively, the printing, cutting and perforating steps could be performed at stations intermediate reel 32 and the stations on the apparatus for which they are required.

By actuating control means 124, strip 38 is fed off reel 32 and downstream of the support 22 until a segment 39 is aligned with the light beam of photoelectric device 54. When this occurs, the signal generated from photoelectric device 54 is directed to control means 124 deactivates stepper motors 72, 78 and 112, whereupon assembly 82 is energized to force tool 88 downwardly to force fiber 20 into the aligned slit 40 directly therebeneath. Simultaneously, cutter blade 120 will be energized to cause the cutting blade to sever the strip at a segment 39, cutting both the strip 38 and fiber 20 which is trapped in the corresponding slit 40 beneath the blade. Then, motors 72, 76 and 112 are then again energized by circuit means 124 after a short time delay, and the strip is moved again downstream until the light beam of device 54 is interrupted once again by the next segment 39. Movement of the tool 88 and cutter blade again occurs. During the movement of strip 38, fiber 20 is being payed out from reel 60 and downwardly to and then along the strip.

Each time the cutting blade severs strip 38, a sheath 18 is formed with a length of fiber 20 between the two halves of the sheath as shown in Figs. 1A and 11. After the sheath containing a fiber length 20 is formed by the cutting action of the cutting blade, the sheath and its fiber length are moved through another machine near the downstream end of support 22. This machine supplies the foil members 14 and 16 with the sheath sandwiched between the foil members as shown in FIG. 12. The outer peripheries of foil members 14 and 16 are heat sealed about a rectangular zone as shown in dashed lines in FIG. 12, whereby package 12 is completed and is ready for shipment, storage or end use.

We claim:

1. Apparatus for use in forming a package comprised of a pair of outer foil members and a fibercontaining sheath between the foil members with said sheath being formed from a foldable strip having spaced index marks thereon and a slit adjacent to each index mark, respectively, said apparatus comprising:

an elongated support;
means on the support for providing a rigid strip folded along its length into two parts;
means on the support for guiding the folded strip for movement along a path adjacent to and longitudinally of the support;
means on the support for incrementally moving the strip along said path;
means on the support adjacent to at least a portion of said path for holding the parts of the strip separated from each other;

means on the support for feeding a flexible fiber into the space between the parts of the strip as the strip is moved along said path and as the parts of the strip are separated from each other;

means on the support for forcing a portion of the fiber into each slit of the strip;

means on the support for cutting the strip and the fiber at each of the index marks thereon, whereby successive cuts of the strip cause a plurality of fiber-containing sheaths to be formed.

2. Apparatus as set forth in claim 1, wherein is included means adjacent to the support for enclosing each sheath, respectively, between a pair of foil members.

3. Apparatus as set forth in claim 1, wherein said strip providing means includes a reel rotatably mounted on the support near one end thereof, said reel adapted to mount the strip thereon in roll form and with the strip being unfolded.

4. Apparatus as set forth in claim 3, wherein said strip providing means further includes a device for folding the strip into said parts as the strip moves off said reel.

5. Apparatus as set forth in claim 1, wherein said strip providing means is adjacent to one end of the support, said strip moving means being adjacent to the opposite end of the support.

6. Apparatus as set forth in claim 1, wherein said means for holding the parts of the strip separated from each other includes a guide on the support adjacent to said path of travel of the strip.

7. Apparatus as set forth in claim 4, wherein said assembly includes a first guide member for orienting one part of the strip in a generally vertical position and the other part of the strip in a generally horizontal position.

8. Apparatus as set forth in claim 1, wherein is included means responsive to the position of an index mark on the strip to deactuate said moving means and thereby interrupt the movement of the strip along said path 9. Apparatus as set forth in claim 1, wherein said forcing means and said cutting means are actuated when the movement of the strip has been interrupted 10. Apparatus as set forth in claim 1, wherein is included control means responsive to the interruption of the movement of the strip for actuating said forcing means and said cutting means.

11. Apparatus as set forth in claim 10, wherein said control means is operable to cause said drive means to be actuated to move the strip after a time delay following the interruption of the movement of the strip along the path.

12. Apparatus as set forth in claim 1, wherein said forcing means includes a tool having means for mounting the tool for up and down movement relative to the support, and means coupled with the tool for moving the same up and down relative to the support.

13. Apparatus as set forth in claim 12, wherein the tool has a lower end provided with an inverted U-shaped configuration, whereby the tool can straddle the fiber and force it into the slit when the slit is aligned with the tool 14. Apparatus as set forth in claim 1, wherein said feeding means includes a reel adapted to mount the fiber thereon in a form of a roll, and means coupled with the reel for rotating the same to allow the fiber on the reel to be moved off the reel and into a position extending along the path of said strip.

15. Apparatus as set forth in claim 14, wherein the reel is above said path of the strip.

16. Apparatus as set forth in claim 9, wherein is included a guide roller adjacent to the path of travel of the fiber off the reel, said roller being rotatable at a tangential velocity greater than that of the reel.

17. Apparatus as set forth in claim 1, wherein is included guide means for moving the parts of the strip together into juxtaposition with each other after the fiber has been placed in the space between the parts.

18. Apparatus as set forth in claim 17, wherein said cutting means is downstream of guide means.

19. Apparatus as set forth in claim 1, wherein said cutting means includes a shaft having a cutter blade on the lower end thereof, and means for moving the shaft downwardly relative to said support.

20. A method for use in forming a package having a pair of outer foil members and a fiber-containing sheath between the foil members, said method comprising:

providing a rigid strip folded along its length into two parts;

moving the strip along a predetermined path;

holding the two parts of the strip separated from each other;

feeding a flexible fiber into a position between the parts of the strip;

releasably securing the fiber to the strip at spaced locations therein, and;

cutting the strip and the fiber at each of said locations on the strip, whereby successive cuts of the strip form a plurality of fiber-containing sheaths having a first side joined by a fold along its length to a second side opposite said first side which is freely moveable.

21. A method as set forth in claim 20, wherein the strip is moved incrementally along said path, said step of holding the parts separated occurring when the strip is moving along said path.

22. A method as set forth in claim 21, wherein said feeding step occurs as the strip moves along said path.

23. A method as set forth in claim 21, wherein said securing step occurs when the strip has been stopped along the said path 24. A method as set forth in claim 21, wherein the cutting step occurs when the strip has been stopped along said path.

25. A method as set forth in claim 20, wherein is included the step of enclosing each sheath in a pouch after the sheath has been formed.

26. A method as set forth in claim 25, wherein said enclosing step includes moving a pair of foil members on opposite sides of each sheath, respectively, and heat sealing the outer peripheral margins of the foil members together.

27. A method as set forth in claim 20, wherein the step of providing said strip includes presenting the strip in the form of a roll, and unrolling the strip from the roll.

28. A method as set forth in claim 27, wherein is included the step of folding the strip as it comes off the roll.

29. A method as set forth in claim 20, wherein the strip moving step includes shifting the strip with one part in a generally vertical position and the other part in a generally horizontal position.

30. A method as set forth in claim 29, wherein said feeding step occurs when the parts of the strip are in said positions.

31. A method as set forth in claim 20, wherein the strip has a plurality of equally spaced index marks thereon, said movement of the strip being interrupted as the function of the positions of the index marks relative to a predetermined reference along said path.

32. A method as set forth in claim 20, wherein the fiber securing step includes penetrating the strip with the fiber, and frictionally holding the fiber in the strip.

33. A method as set forth in claim 32, wherein the strip has a slit therein at each of said locations, respectively, said penetrating step includes forcing the fiber into each slit.

34. A method as set forth in claim 20, wherein the step of feeding the fiber includes unreeling the fiber from a station above the path of travel of the strip.

35. A method as set forth in claim 20, wherein the strip is cut when the two parts of the strip are juxtaposed and the fiber is held between the parts of the strip.

* * * * *